(12) United States Patent
Dinsa

(10) Patent No.: US 9,683,919 B2
(45) Date of Patent: Jun. 20, 2017

(54) VISCOMETER CELL ATTACHMENT DEVICE

(71) Applicant: Harpreet Singh Dinsa, Calgary (CA)

(72) Inventor: Harpreet Singh Dinsa, Calgary (CA)

( * ) Notice: Subject to any disclaimer, the term of this patent is extended or adjusted under 35 U.S.C. 154(b) by 154 days.

(21) Appl. No.: 14/608,601

(22) Filed: Jan. 29, 2015

(65) Prior Publication Data

US 2015/0211963 A1    Jul. 30, 2015

Related U.S. Application Data

(60) Provisional application No. 61/933,462, filed on Jan. 30, 2014, provisional application No. 61/943,812, filed on Feb. 24, 2014.

(51) Int. Cl.
G01N 11/04    (2006.01)
G01N 11/08    (2006.01)

(52) U.S. Cl.
CPC ............. *G01N 11/04* (2013.01); *G01N 11/08* (2013.01)

(58) Field of Classification Search
CPC .................. G01N 11/04; G01N 11/08; G01N 11/10–11/12
See application file for complete search history.

(56) References Cited

U.S. PATENT DOCUMENTS

| 3,930,403 | A | * | 1/1976 | Cross | G01N 11/04 417/393 |
|---|---|---|---|---|---|
| 4,643,020 | A | | 2/1987 | Heinz | |
| 4,890,482 | A | | 1/1990 | Maini | |
| 5,932,800 | A | | 8/1999 | Cummings | |
| 6,807,849 | B1 | * | 10/2004 | Reed | G01N 11/14 73/54.28 |
| 9,297,255 | B2 | * | 3/2016 | Gao | E21B 49/081 |
| 2002/0029806 | A1 | * | 3/2002 | Giordano | G05D 16/106 137/509 |
| 2011/0185809 | A1 | * | 8/2011 | Guieze | G01N 1/2202 73/32 R |
| 2013/0199286 | A1 | * | 8/2013 | Gao | E21B 49/081 73/152.27 |
| 2014/0102188 | A1 | * | 4/2014 | Murphy | G01N 33/2823 73/152.05 |

OTHER PUBLICATIONS http://www.chandlerengineering.com/Products/Reservoir%20Analysis/Model2347.aspx; Chandler Engineering Model 2347 Floating Piston; Received & Printed Oct. 14, 2014.

* cited by examiner

*Primary Examiner* — Natalie Huls
(74) *Attorney, Agent, or Firm* — Neustel Law Offices

(57) ABSTRACT

A viscometer cell attachment device which greatly improves efficiency, accuracy, precision, and safety when testing viscosity of a substance with a viscometer. The viscometer cell attachment device generally allows dangerous, high pressure, potentially explosive/flammable methane/fluids in a viscometer cell to be partially removed and contained safely, sheared by a constriction member, generally comprised of a length of OD tubing, which generates foams/emulsions, and then put back in the viscometer cell. The invention can be attached to some types of viscometers. It can handle methane safely and can be used to produce homogeneous methane/fluids foams/emulsions by repeating the process.

19 Claims, 18 Drawing Sheets

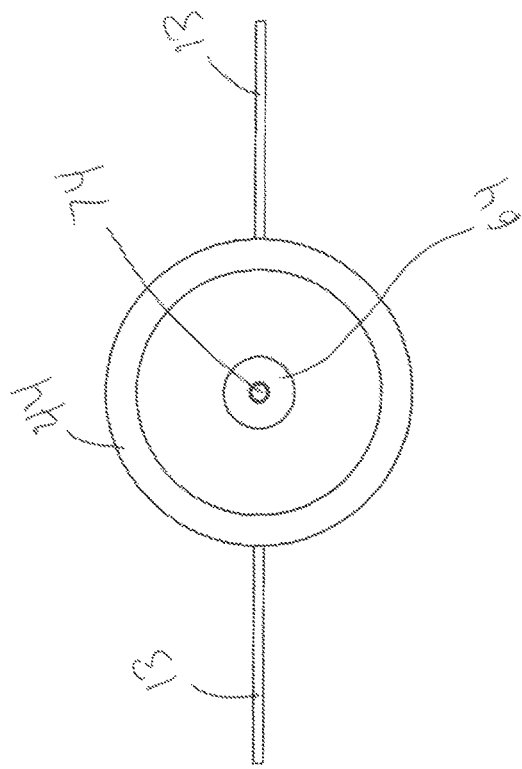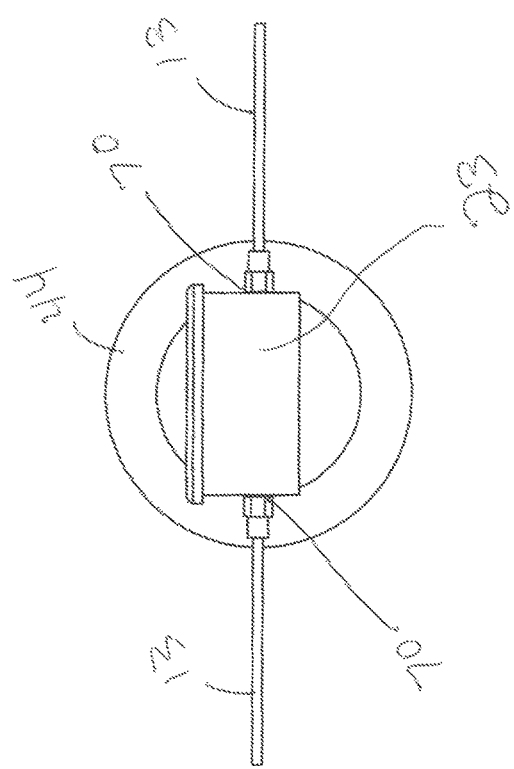

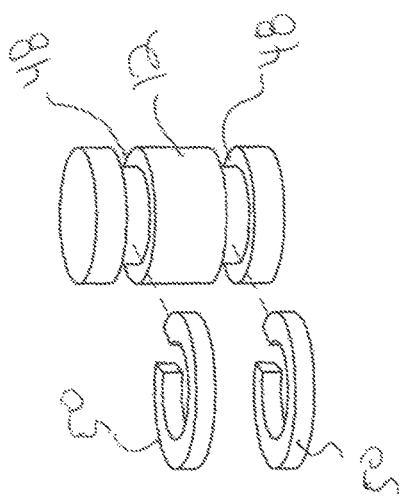
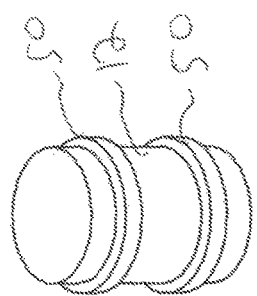
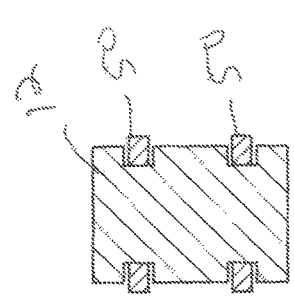
FIG. 9a
FIG. 9b
FIG. 9c

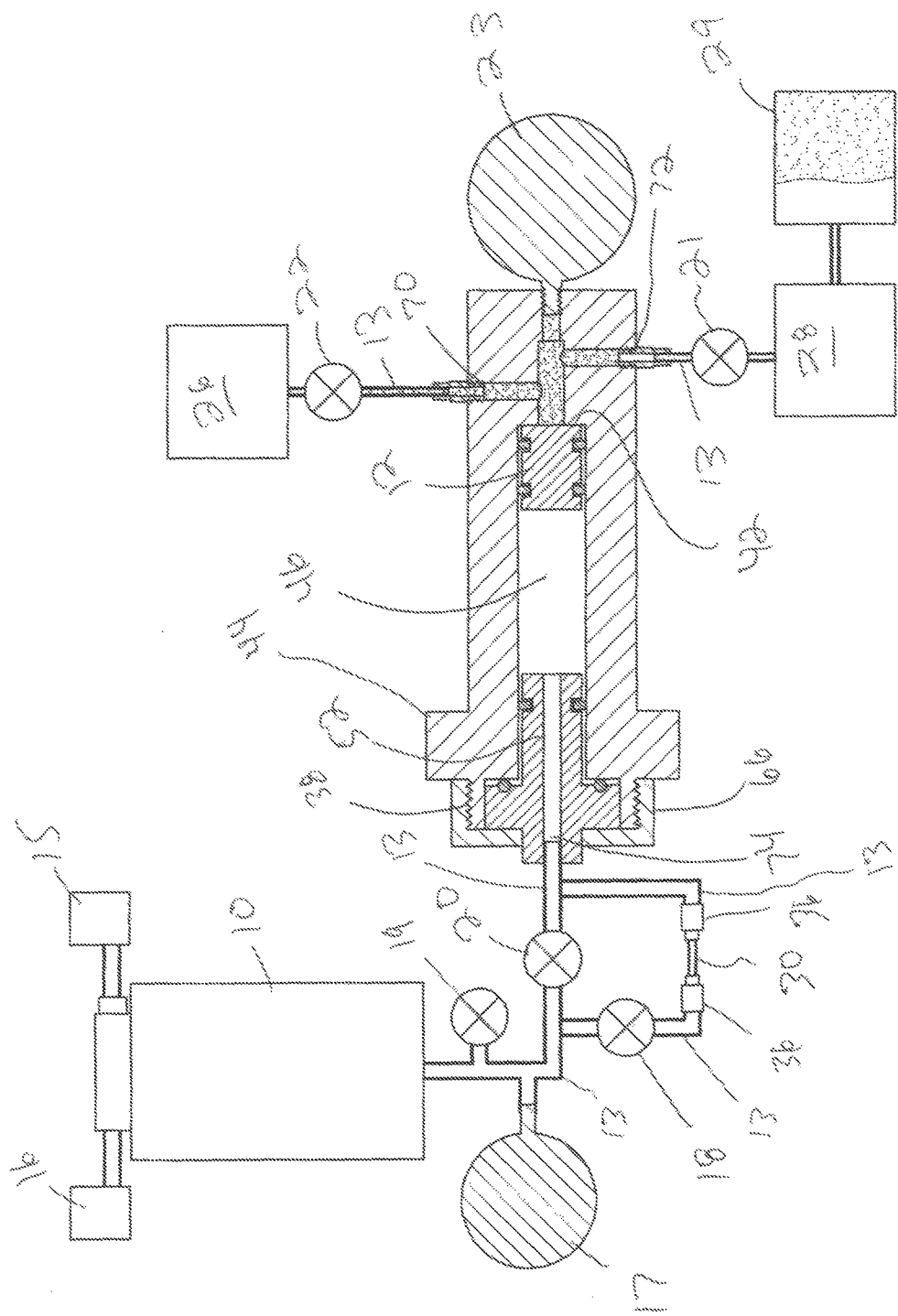

VISCOMETER CELL ATTACHMENT DEVICE

CROSS REFERENCE TO RELATED APPLICATIONS

I hereby claim benefit under Title 35, United States Code, Section 119(e) of U.S. provisional patent application Ser. No. 61/933,462 filed Jan. 30, 2014. The 61/933,462 application is hereby incorporated by reference into this application.

I hereby claim benefit under Title 35, United States Code, Section 119(e) of U.S. provisional patent application Ser. No. 61/943,812 filed Feb. 24, 2014. The 61/943,812 application is hereby incorporated by reference into this application.

STATEMENT REGARDING FEDERALLY SPONSORED RESEARCH OR DEVELOPMENT

Not applicable to this application.

BACKGROUND OF THE INVENTION

Field of the Invention

The present invention relates generally to a viscometer attachment and more specifically it relates to a Viscometer Cell Attachment Device which greatly improves efficiency, accuracy, precision, and safety when testing viscosity of a substance with a viscometer.

Description of the Related Art

Any discussion of the related art throughout the specification should in no way be considered as an admission that such related art is widely known or forms part of common general knowledge in the field.

Viscometer cells are commonly used for various purposes, such as by laboratory equipment manufacturers for sale or by oil well service companies that pump fracks. One such viscometer cell used is the PC-10 viscometer. Its cell has a simple internal mixer for generation of methane/fluids/foams/emulsions for viscosity testing.

The present invention attached to a newer viscometer is better at measuring viscosity, much safer for the operator and shears more than simple mixing. The PC-10 cell 'plug' has a large surface area and is subjected to great forces; and has only one polypack seal. A leak can also occur at the magnet cap polypack seal. Pressure and forces climb when the PC-10 cell is heated to high temperatures. Gels under pressure will contaminate the PC-10 magnet giving erroneous viscosity readings. The invention is not heated. Otherwise, there is nothing on the market that does what the invention does as viscosity testing of methane/fluids foams/emulsions is not common.

With the present invention, a user is able to connect their existing pressurized viscometer keeping costs down to test the viscosity of methane fluids foams/emulsions. The present invention is a closed system when equipped with a pressure release tank (may use empty methane tank), has one moving part, is overbuilt and has backup seals making it a very safe way to handle and generate methane fluids foams/emulsions Because of the inherent problems with the related art, there is a need for a new viscometer cell attachment device which greatly improves efficiency, accuracy, precision, and safety when testing viscosity of a substance with a viscometer.

BRIEF SUMMARY OF THE INVENTION

The invention generally relates to a viscometer attachment which allows dangerous, high pressure, potentially explosive/flammable methane/fluids in a viscometer cell to be partially removed and contained safely, sheared with a nozzle which generates foams/emulsions, and then put back in the viscometer cell. The invention can be attached to some types of viscometers. It can handle methane safely and can be used to produce homogeneous methane/fluids foams/emulsions by repeating the process.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 6 is a frontal view of the present invention.

FIG. 7 is a rear view of the present invention.

FIG. 9a is an upper perspective view of the piston of the present invention with polypack seals removed.

FIG. 9b is an upper perspective view of the piston of the present invention with polypack seals connected.

FIG. 9c is a sectional view of the piston of the present invention.

FIG. 12 is a sectional view of the present invention connected to a viscometer cell.

DETAILED DESCRIPTION OF THE INVENTION

A. Overview

Figure 1:
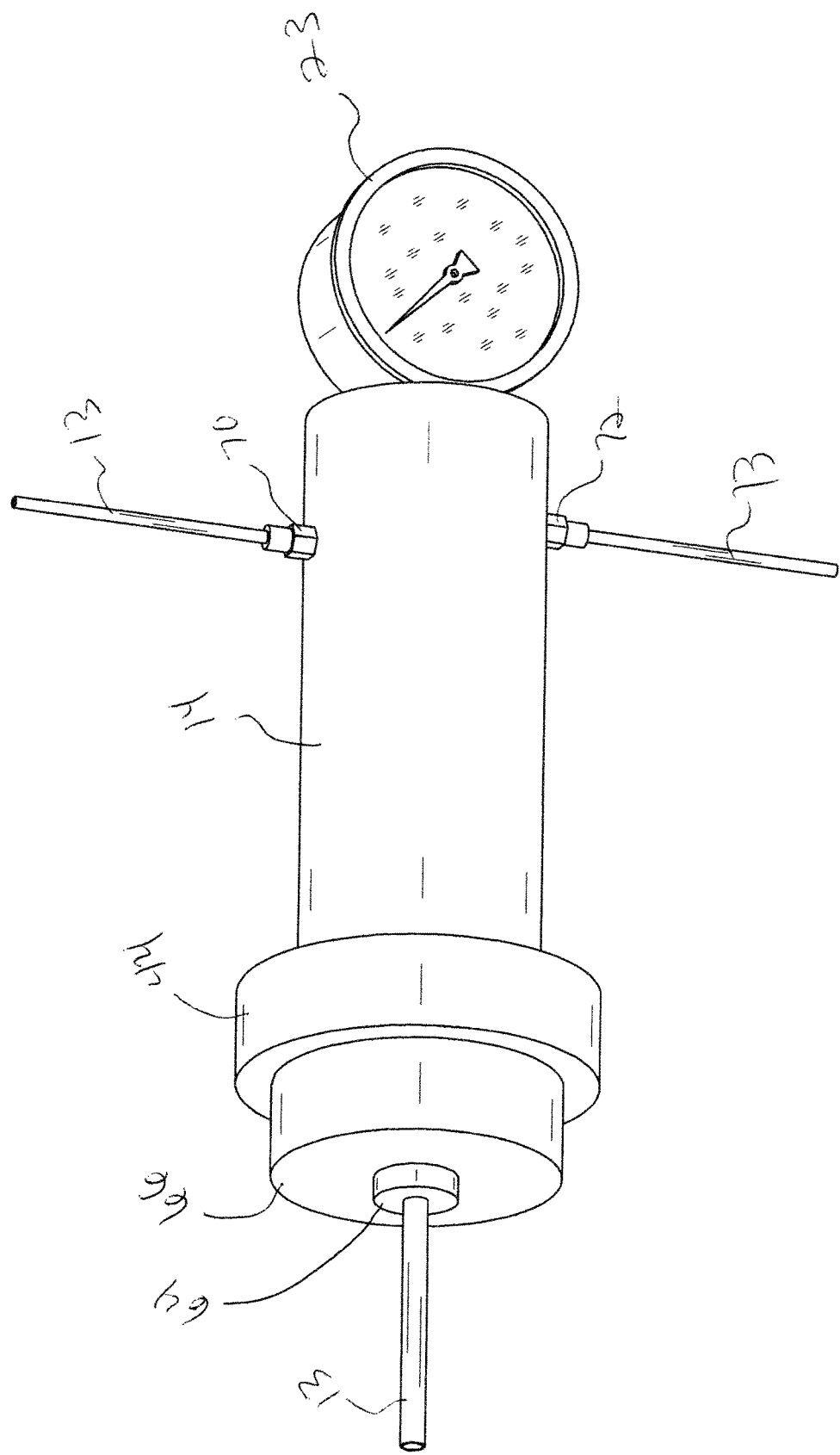
FIG. 1 is an upper perspective view of the present invention.

Turning now descriptively to the drawings, in which similar reference characters denote similar elements throughout the several views, FIGS. 1 through 19 illustrate a viscometer cell attachment device, which allows dangerous, high pressure, potentially explosive/flammable methane/fluids in a viscometer cell 10 to be partially removed and contained safely, sheared by a constriction member, generally comprised of a length of OD tubing, which generates foams/emulsions, and then put back in the viscometer cell 10. The invention can be attached to some types of viscometers 10. It can handle methane safely and can be used to produce homogeneous methane/fluids foams/emulsions by repeating the process.

As shown throughout the figures, the present invention is an attachment for high pressure viscometer cells 10. The present invention is not only a foams/emulsions generator that pushes methane/fluids through a constriction member 30, but also functions to remove and safely contain methane/fluids in the piston cell 14 so that they can be sheared and pushed back into the viscometer cell.

The main body of the piston cell 14 of the present invention may be comprised of various configurations. In a preferred embodiment, the piston cell 14 is made from a single piece of 316 stainless steel (as are the piston 12, plug 52 and lid 66). However, the scope of the present invention should not be construed as limited in this respect, as various other materials may be utilized for the piston cell 14 in alternate embodiments.

Figure 8:
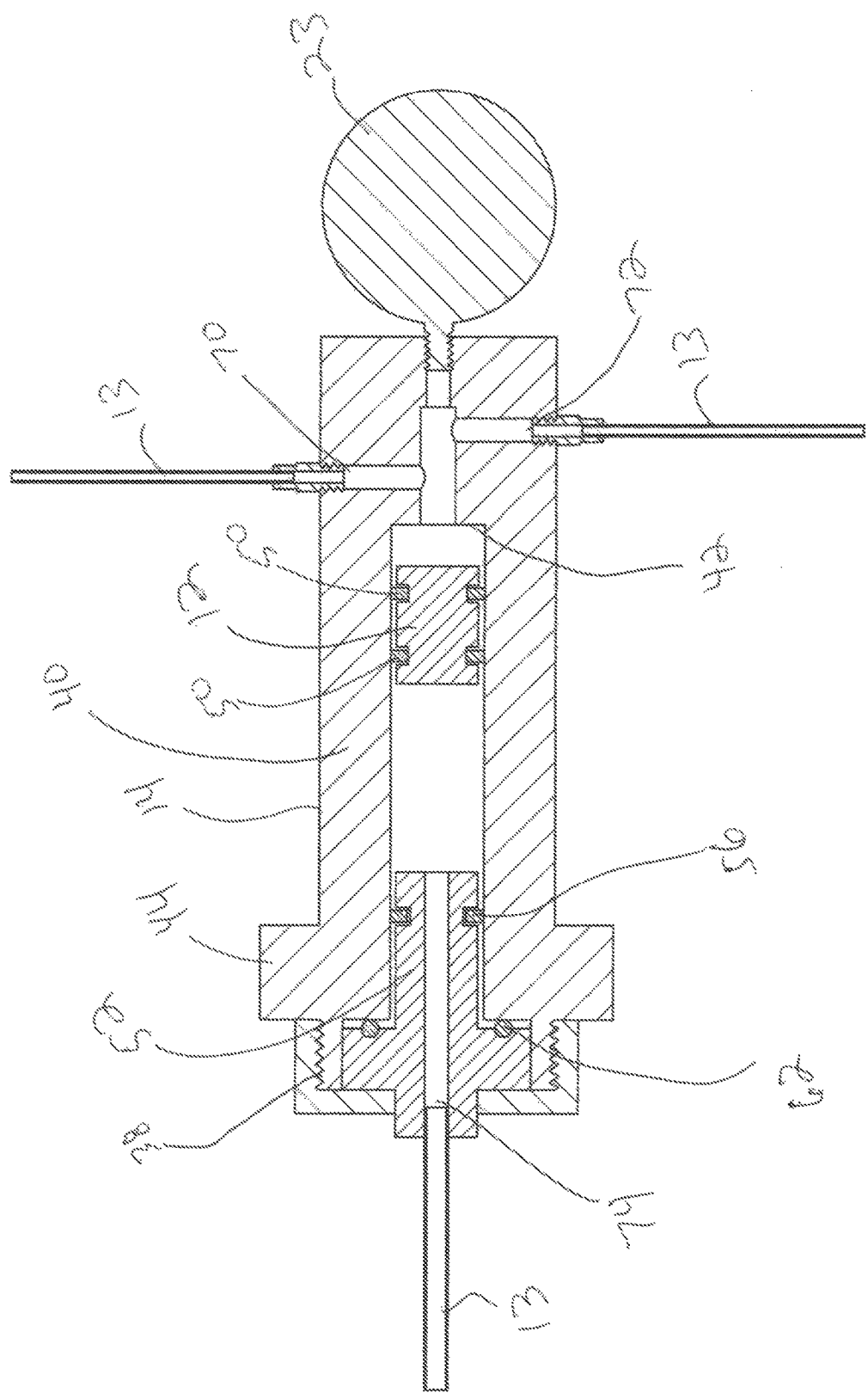
FIG. 8 is a sectional view of the present invention.

As best shown in FIG. 8, the piston cell 14 generally includes an open end and a closed end. The closed end contains the piston stop 42 which creates a cellar 46 having one or more ports 68, 70, 72, 74. In a preferred embodiment, three ports 68, 70, 72 will be utilized in the piston cell 14. The first port 68 in such a preferred embodiment will be adapted for connection to a pressure gauge 23. The second port 70 (configured for fitting, tubing and needle valve) is adapted to be connected to a pressure release tank 26. This configuration is used to contain any residual fluid in the cell 14 when the piston 12 is pushed against its stop 42 or for containing a methane leak if the piston polypack seals 50 fail. The third port 74 (configured for fitting, tubing and needle valve) is adapted to be connected to a pump 28 to allow a pumped fluid such as water, mineral oil, or pressurized gas to enter and push the piston 12.

Figure 10A:
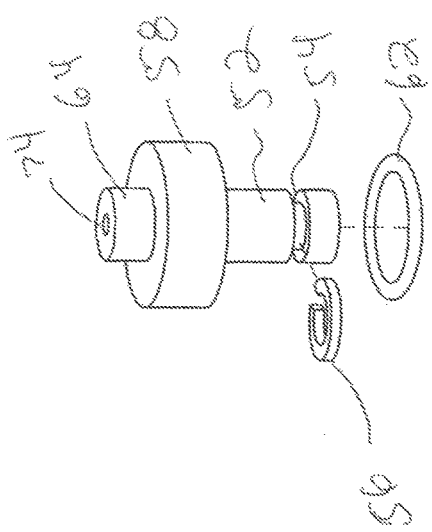
FIG. 10a is an upper perspective view of the cell plug of the present invention with O-ring seal and polypack seal removed.
Figure 10B:
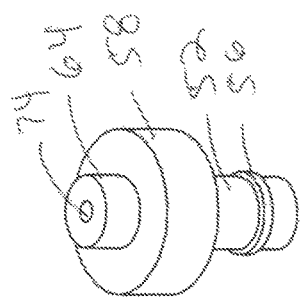
FIG. 10b is an upper perspective view of the cell plug of the present invention with the O-ring seal and polypack seal connected.
Figure 10C:
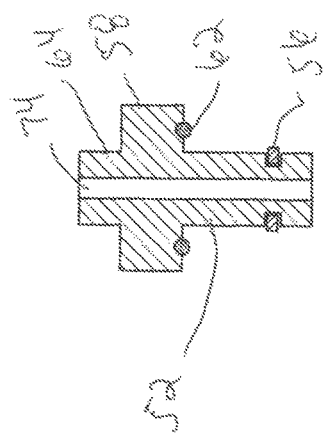
FIG. 10c is a sectional view of the cell plug of the present invention.
Figure 11A:
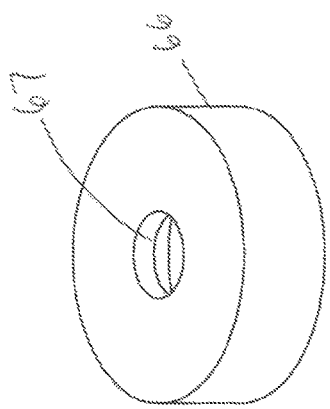
FIG. 11a is an upper perspective view of the lid of the present invention.
Figure 11B:
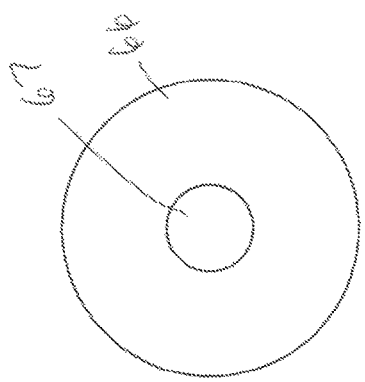
FIG. 11b is a top view of the lid of the present invention.
Figure 11C:
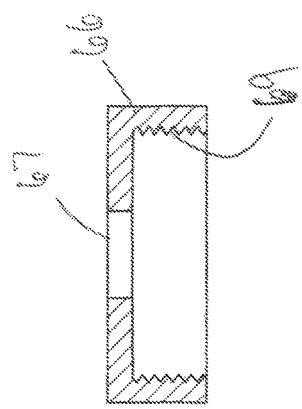
FIG. 11c is a sectional view of the lid of the present invention.
Figure 13:
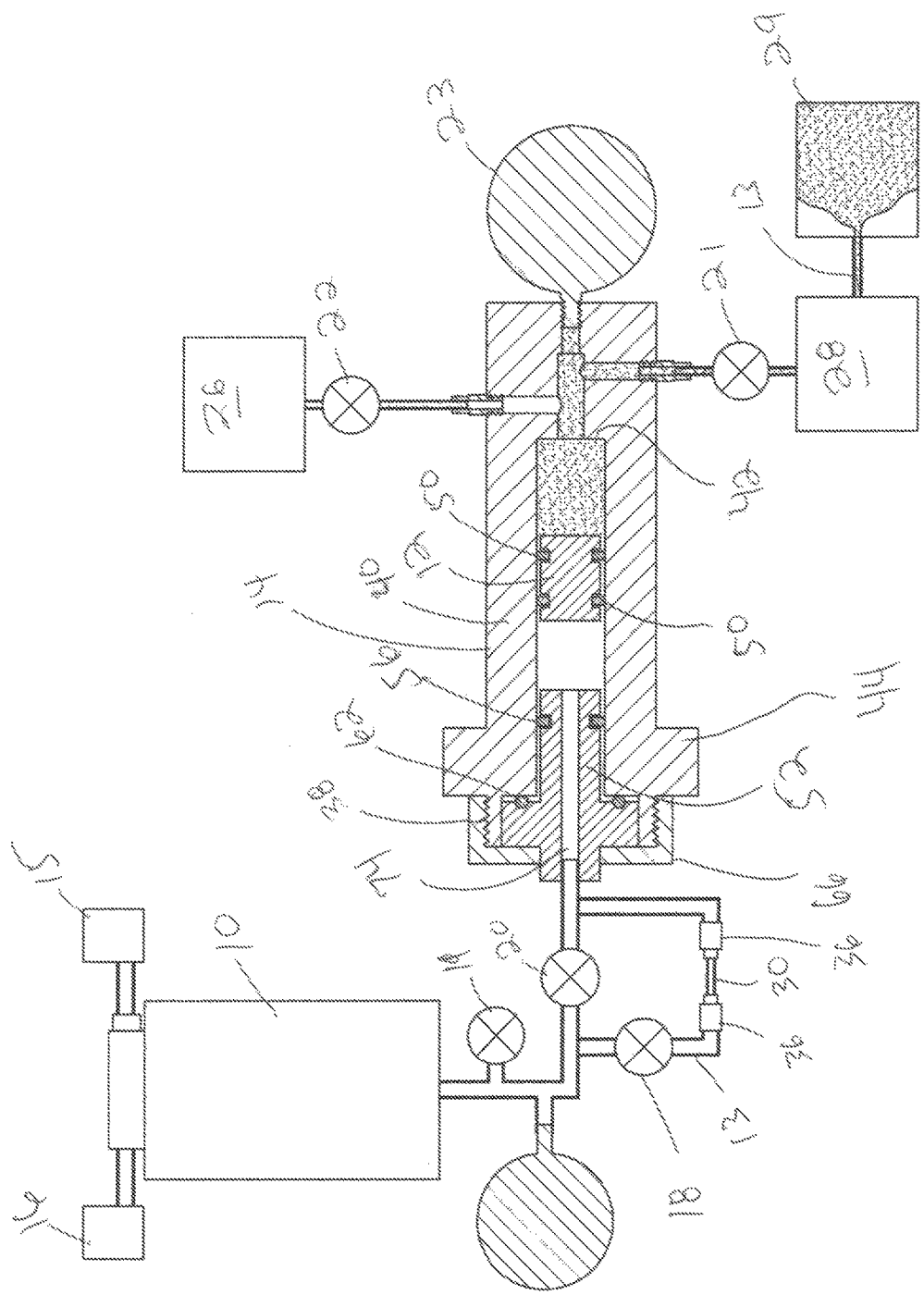
FIG. 13 is a sectional view of the present invention in use.
Figure 14:
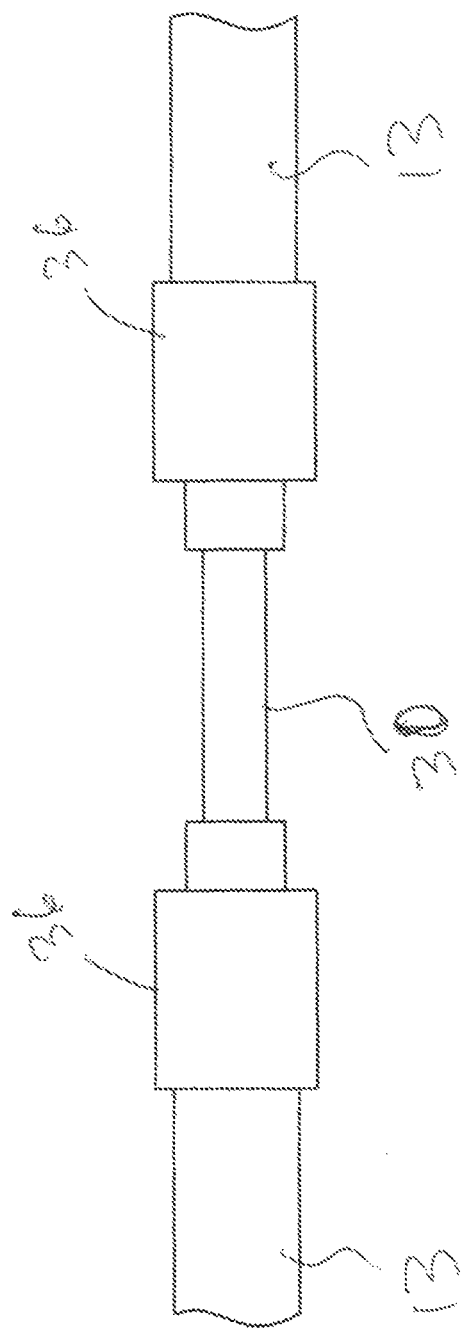
FIG. 14 is a frontal view of the constriction member of the present invention.

As best shown in FIGS. 10a, 10b, and 10c, the cell plug 52 provides a positive, redundant sealing by using both a polypack seal 56 and an O-ring seal 62 so that methane gas is unlikely to escape. The open end of the cell 14 is for removing the piston 12 when its polypack seals 50 need to be replaced. The open end of the cell 14 also allows replacement of the polypack seal 56 and an O-ring seal 62 for the cell plug 52.

Figure 5:
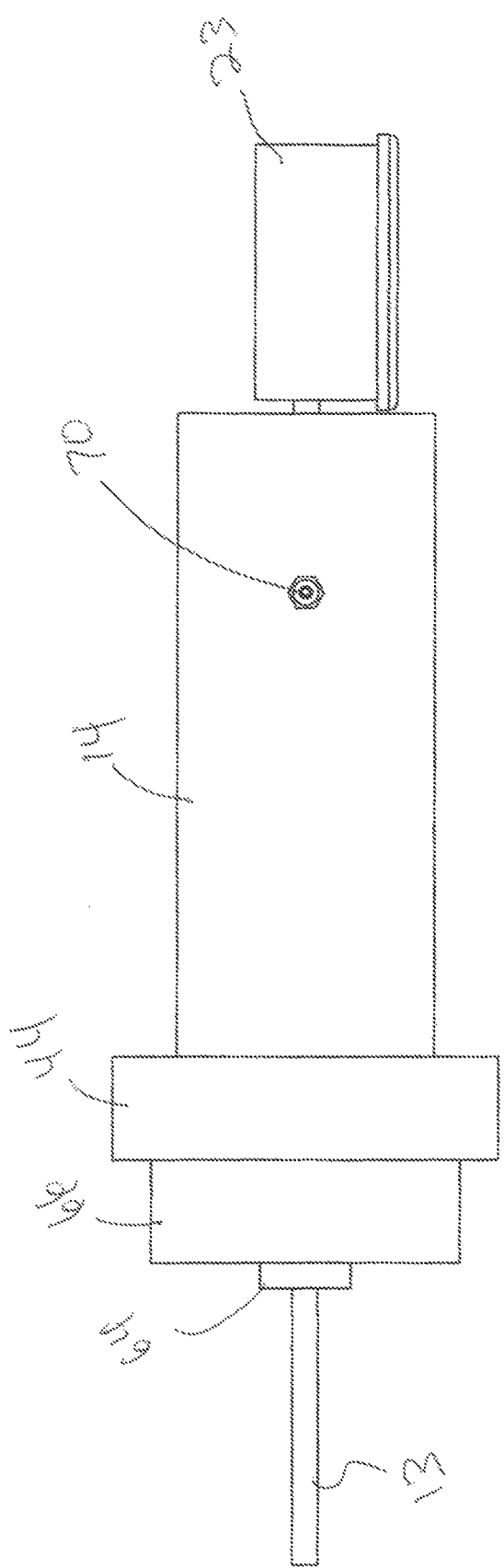
FIG. 5 is a second side view of the present invention.

The cell plug 52 utilizes a lid 66 to aid in containing the high pressure methane such as the large donut shaped screw-on lid 66 as shown in FIG. 5. The main cell collar 44 provides extra strength and durability for large, strong threads 38 to hold the screw-on lid 66 tightly in place. The cell collar 44 may be comprised of various materials, such as stainless steel.

The only moving part utilized in the present invention is the piston 12. This reduces the likelihood of methane leaks, particularly with a pressure release tank. Again, redundancy has been built into the design of the apparatus making it a safe tool for handling methane.

As shown in FIG. 10b, the top of the cell plug 52 has a port 74 so that fluids/gases may enter and leave the piston cell 14. The constriction member 30 with a reducing union 36 and tube OD fittings generates substantial shear to create stable, homogeneous methane foams/emulsions. This cannot be accomplished in a single piston cycle, so a few cycles of the piston 12 are required.

There are two pressure gauges 17, 23 on the apparatus that are positioned to measure pressure on each side of the piston 12. The same reading on both the pressure gauges 17, 23 is a warning that the piston polypack seals 50 have been compromised.

The apparatus may be plumbed in various configurations. In one embodiment shown in FIG. 1, the apparatus is plumbed using high pressure (15000 psi working pressure) SS ¼" OD tubing with a tube wall thickness of 0.049" and high pressure (15000-20000 psi) SS ¼" Swagelok fittings. The apparatus may include a plurality of needle valves 18, 19, 20, 21, 22, such as five high pressure SS (15000 psi) ¼" female NPT needle valves as shown. In some embodiments, the valves 18, 19, 20, 21, 22 may be electrically actuated (i.e. controlled electronically with or without the aid of computer software, which may also be used to control the direction of fluid flow into and out of the invention).

There are generally two valves 21, 22 on the closed end of the piston cell 14 as shown in FIG. 12, which, as described above, are for the pressure release tank 26 and for the entry of fluids pumped by the pump. The open end of the piston cell 14 may include one or more valves 18, 19, 20 as shown in FIG. 12. In one embodiment, there are three valves 18, 19, 20 attached with tubing and fittings to the open end of the cell 14.

A first valve 18 may be utilized to control flow through the constriction member 30. The second valve 18 is closed when the viscometer cell 10 is initially being filled with methane or to hold pressure in the viscometer cell 10 when the viscosity of the methane foams/emulsions is being tested. A second valve 19 is for a methane tank 16 which is required to initially pressure up the viscometer cell 10 if it only has one port for entry and exit of fluids. Once the viscometer cell 10 is pressured up with methane, the second valve 19 remains closed.

A third valve 20 may be utilized to regulate flow through the OD tubing 13 (tubing without a constriction member 30 or nozzle) and to provide a direct path for methane and especially the other fluids (hydrocarbon gels or water gels) in the viscometer cell 10 to move more completely from the viscometer cell 10 to the piston cell 14. When pushing methane/fluids in the other direction the third valve 20 is closed so that methane/fluids are forced through the constriction member 30 only. Like the nozzle needle valve 18, it is also closed when the viscometer cell is initially being filled with methane or to hold pressure in the viscometer cell 10 when the viscosity of the methane foams/emulsions are being tested. Needle valves 17, 18, 19 are open and shut to direct flow.

All the parts of the invention work together to move methane/fluids from a viscometer cell 10 into a piston cell 14, which are then forced through a shearing constriction member 30 and replaced back in the viscometer cell 10 mixed. Omission of various components of the present invention may compromise its functionality. For example, the piston 12 would not work without the polypack seals 50 and the cell plug 52 would not work if both its polypack 56 and O-ring seal 62 were missing. Also, the cell plug 52 would not work if there was no lid 66 to hold the plug in place. The invention is designed to be very simple and there are no extraneous components or features. Even the piston cell 14 generally only has one open end to reduce the chance of leaks past seals.

The present invention's simplicity improves safety, which is paramount when working with methane that can be flammable/explosive and is an asphyxiant. The simple design allows the present invention to be overbuilt with beefy components again improving safety. There are no electrical components that could spark a fire or explosion. There is redundancy built into the system. As discussed above, the cell plug polypack seal 56 is backed by its O-ring seal 62 to improve safety. Also, the pressure release tank 26 will contain the methane if the piston polypack seals 50 fail making a closed system. Finally, with two pressure gauges 17, 23 on each side of the piston, we can actually see if the piston polypack seals 50 have failed. If the pressure gauges 17, 23 are reading the same pressure, it is likely the piston polypack seals 50 have failed. Redundancy contributes to safety.

The tubing 13 and the needle valves 18, 19, 20, 21, 22 especially, all help to shear the methane foams/emulsions. A constriction member 30 provides even more complete shearing. The constriction member 30 may also be interchangeable in some embodiments. A few passes through the constriction member 30 ensures the methane/fluids/foams/emulsions are completely mixed and homogeneous. This is especially true when using high pressure methane as there is much stored energy to move methane/fluids. The vapor pressure of liquid methane at room temperature is 4600 psi. A mixer such as utilized in the prior art will not provide near as much shear as the present invention.

A major reason why the invention itself is unique is because methane fracking is not common. There is almost no demand for generating and testing the viscosity of methane/fluids foams/emulsions. The invented apparatus capitalizes on the high pressure (more stored energy) properties of liquid methane especially, to move fluids. This is a very safe and yet cost effective invention for testing high pressure and potentially explosive/flammable fluids, especially methane. The operator will feel & be safe. It is much safer and develops more shear than a PC-10 viscometer 10 equipped with an internal mixer. The invention can be adapted to some viscometers on the market because it only requires one port to work. The invention can work with smaller sample sizes by scaling down the piston cell 14 dimensions and using smaller high pressure ⅛" OD tubing 13, fittings and needle valves 18, 19, 20, 21, 22. The invention is not simply a foams/emulsion generator, but also functions to safely move methane/fluids out of a viscometer cell 10, into a piston cell 14 and back through a constriction member 30 into the viscometer cell 10.

B. Description of Parts

The main body of the piston cell 14 may include threading 38 such as the coarse threads 38 shown at the open end of the cell 14. The piston cell 14 may be machined from a single piece of cylindrical 316 stainless steel, or may be comprised of other materials.

The walls 40 of the piston cell 14 may be comprised of various thicknesses to accommodate different functionality. In one embodiment, the cell walls 40 are ½" thick and the piston stop 42 has a wall thickness of ¾". Below the 1" high coarse threads 38 at the open end of the cell there may be a 1" high cell collar 44 with a wall thickness of 1" in such an embodiment.

The shade-filled area in FIG. 8 is a side cut-out view of the single piece cell body 14. The cell bore may include a 1" ID and at the piston stop 42 it may be ½" ID. The stop serves to limit the piston movement to create a cellar 46.

The overall length of the cell 14 is determined by the volume of the viscometer cell 10 used. The viscometer cell 10 and piston cell 14 volume should be similar. In the event the viscometer cell 10 has a small volume, the piston cell 14 wall thickness can be maintained and the piston 12 diameter can be reduced. The overall length of the cell 14 can also be reduced and high pressure SS ⅛" OD tubing 13, Swagelok fittings with ⅛" male NPT end connectors and/or ⅛" male tubing end connectors; and ⅛" female NPT needle valves 18, 19, 20, 21, 22 may be used. It should be noted that even smaller sizes are available as well as other types of higher pressure tubing 13, fittings and needle valves 18, 19, 20, 21, 22.

The piston 12 may be comprised of various materials, such as 316 stainless steel. The piston 12 may be comprised of various sizes, such as 1" in diameter and 2" long. Square grooves 48 at each end of the piston 12 allow for polypack seals 50. The polypack seals 50, which may be comprised of viton rubber, face outward from each other. Piston/cell wall tolerances will be tight so that the polypacks 50 seal properly.

The cell plug 52 at the open end of the cell may be various sizes, such as 1" in diameter. The cell plug 52 may also be comprised of various materials, such as 316 stainless steel. The cell plug 52 generally projects 1.5" into the cell and may include a square groove 54 (same as piston) for a polypack seal 56 (same as piston polypack seal) with the same plug/cell wall tolerances as the piston/cell walls.

Figure 2:
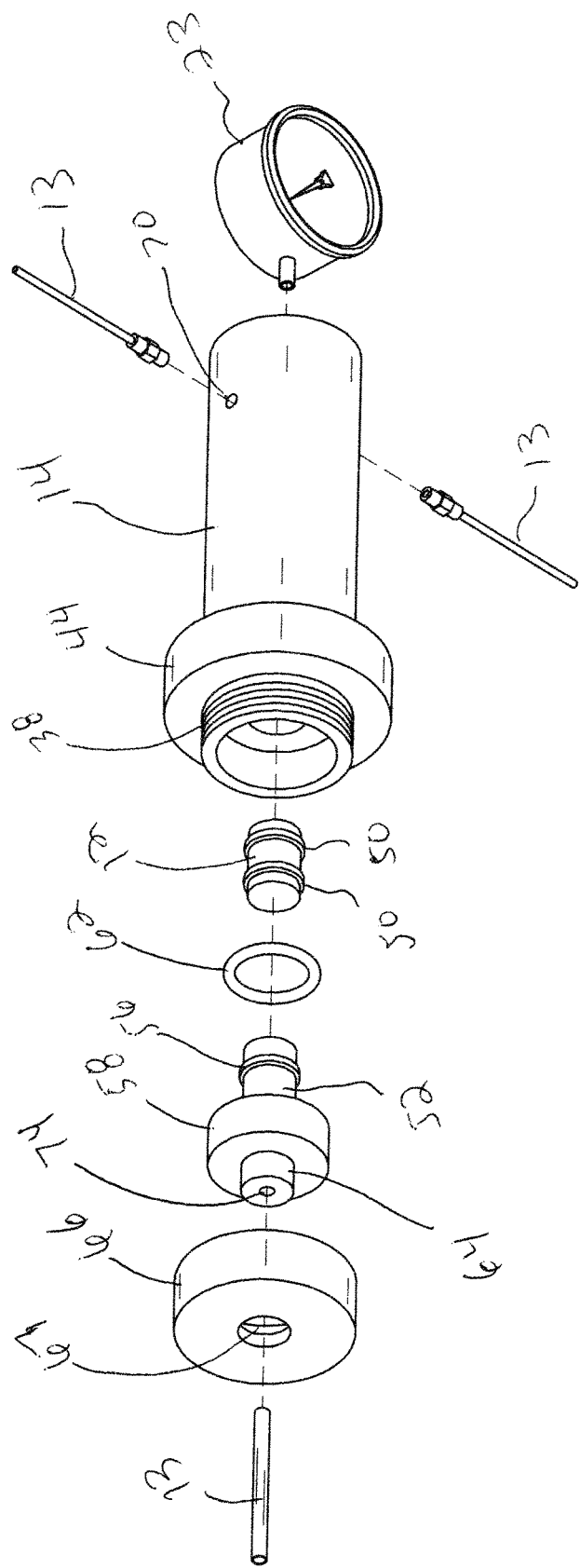
FIG. 2 is an exploded upper perspective view of the present invention.
Figure 3:
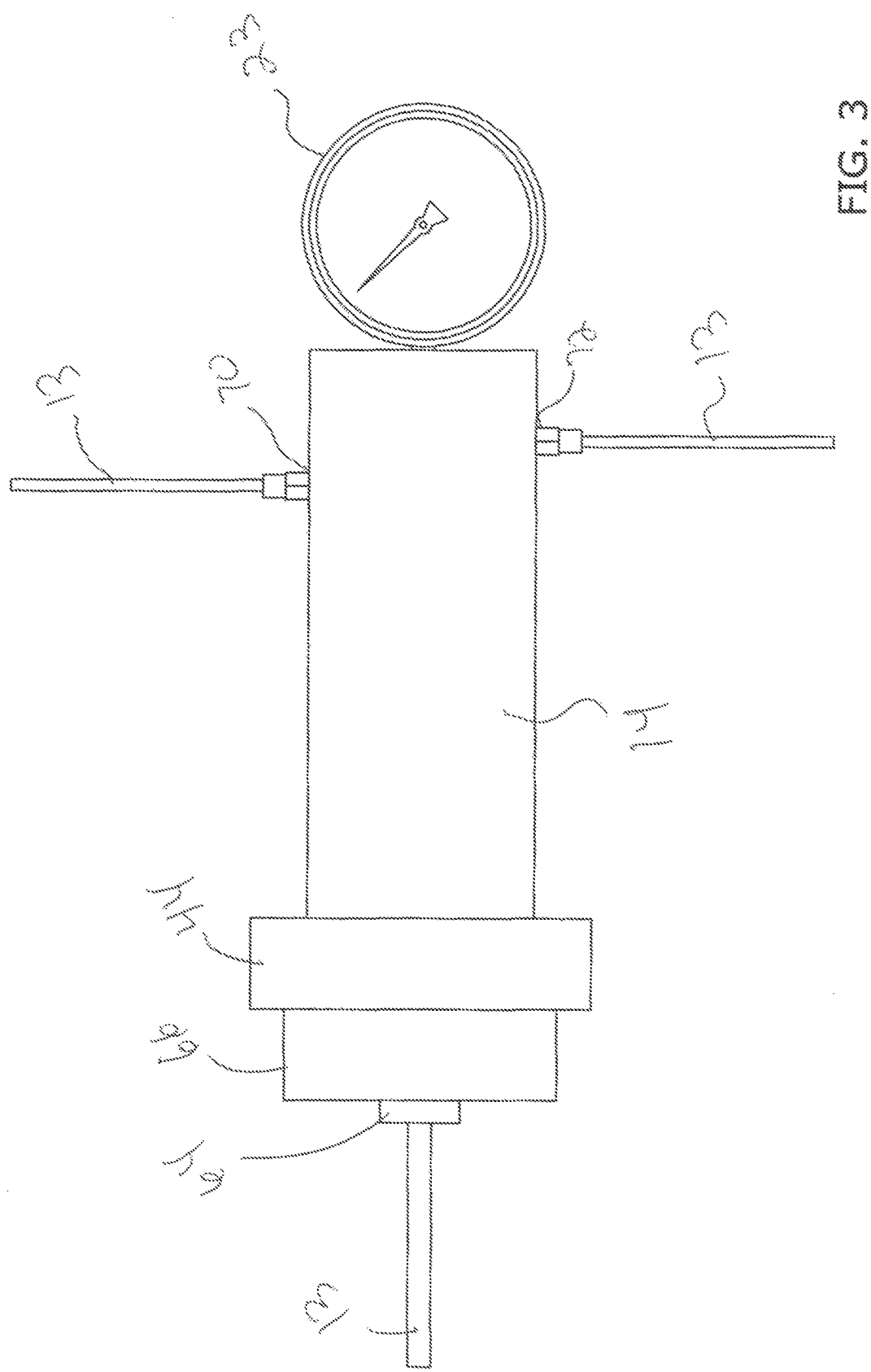
FIG. 3 is a top view of the present invention.
Figure 4:
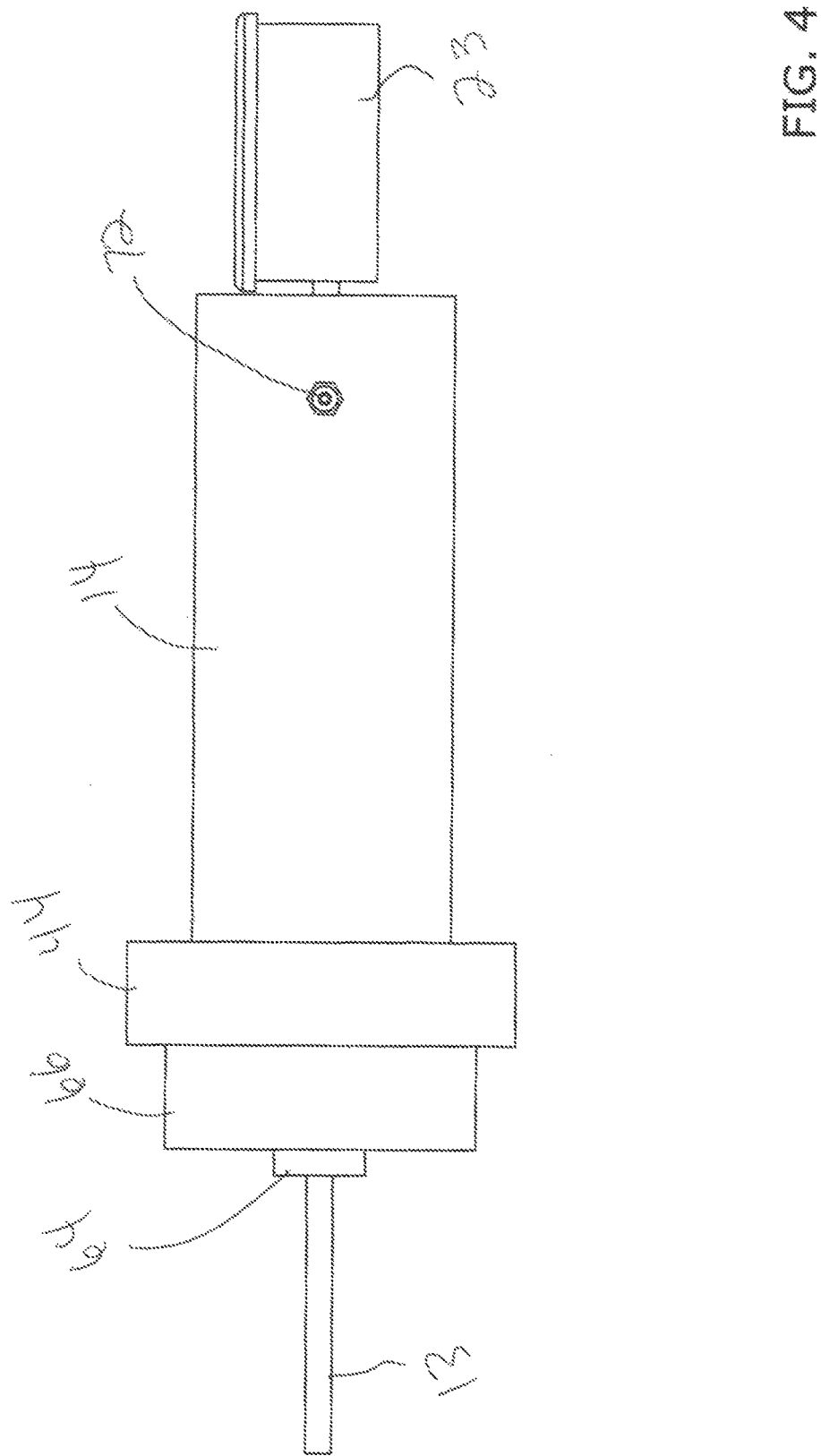
FIG. 4 is a first side view of the present invention.

The cell plug collar 58 may be 1" high so it rests flush with the top of the coarse cell threads. In FIG. 2, it is shown that the cell threads 38 are moved outwardly so as to accommodate the larger diameter plug collar 58 so that it can rest against the existing cell collar 44. At the bottom of the plug collar 58, a semi-circular groove 60 is machined for an O-ring 62 that acts as a secondary back-up seal sandwiched between the base of the plug collar 58 and the top of the main cell collar 44. The o-ring 62 may be comprised of Viton rubber.

The crown 64 on top of the plug may be 1" high and 1" in diameter. It serves as a grasping point to remove the cell plug 52 to change out all the polypack seals 50, 56 and O-ring seal 62. Finally, a coarse threaded, donut shaped, screw on lid 66, which may be machined from a single piece of cylindrical 316 stainless steel, is used to hold the cell plug 52 in place. The lid height may be 1.5" and is screwed all the way down to the top of the main cell collar 44. The lid 66 includes an opening 67 at a central portion thereof for receiving tubing 13. The lid 66 may also include its own threading 69 which connects with the threading 38 of the piston cell 14.

The present invention may include one or more ports 68, 70, 72 which extend through the piston cell 14 into the cellar 46. In an embodiment shown in the figures, three ports 68, 70, 72 (holes) tapped with ¼" NPT threads are drilled through into the cellar 46. The ports 68, 70, 72 are for fittings with a ¼" male NPT connector on one end, at least.

As shown in the exemplary embodiment of the figures, one port 68 is centered on the closed end of the cell and is for a pressure gauge 23. The other two ports 70, 72 are drilled through the sides of the cell 14 into the cellar 46. The second port 70 goes to the pressure release tank 26 (may use empty methane tank from methane supplier) and the third port 72 is for the pump 28.

As shown in FIG. 2, there may be a forth port 74 drilled through the center of the cell plug 52 which is also tapped with ¼" NPT threads. FIG. 1 shows plumbing of high pressure SS ¼" OD tubing, high pressure SS ¼" Swagelok fittings, and high pressure SS ¼" female NPT needle valves (18, 19, 20, 21, 22).

The constriction member 30 is a length of OD tubing. While the constriction member 30 may comprise various sizes, a preferred embodiment comprises a 5" length of ⅛" OD tubing with a wall thickness of 0.035. The constriction member 30 may be replaced by different length of OD tubing with different wall thicknesses for different levels of shear. The constriction member 30 is connected to the existing OD tubing using unions 36 at each end.

C. Fabrication of Present Invention

The larger parts of the piston cell 14 may be machined from cylindrical ingots of 316 stainless steel. This includes the main cell body 14, the piston 12, the cell plug 52 and the cell lid 66. The present invention may be fabricated at a machine shop and put together also using parts purchased directly from suppliers such as tubing, fittings, needle valves 18, 19, 20, 21, 22, seals, pressure release tank 26, pump 28 and pressure gauges 17, 23.

The ports drilled and tapped with ¼" NPT threads (to accept fittings with a ¼" male NPT connector) include the three ports 68, 70, 72 going into the cell cellar 46 for the pressure release tank 26, pump 28 and pressure gauge 23 and the port 74 drilled through the top of the cell plug.

D. Operation of Preferred Embodiment

To operate the present invention it is necessary to understand how it works so that the valves 18, 19, 20, 21, 22 can be properly manipulated to direct fluid/gas flow. The present invention is not simply a pump, but is equipped with other components such as valves 18, 19, 20, 21, 22, pressure gauges 17, 23 and a constriction member 30 for shearing.

The valves 18, 19, 20, 21, 22 must be properly manipulated to direct methane/fluids flow through the constriction member 30. The pressure gauges 17, 23 must be interpreted correctly to know what the apparatus is doing. The invention is designed to be simple and only has one moving part, the piston. This also makes it safer, more reliable, durable, less costly and less costly to maintain.

The present invention is the only viable and safest solution for working with high pressure and dangerous methane, short of creating a cost prohibiting explosion proof chamber. The present invention has no electrical components so there is no danger of a spark originating from it. The piston cell 14 has only one open end for methane to escape requiring less seals. The simple design makes it easy to over build.

The present invention has redundant features built into it to maximize safety when working with methane. The cell plug 52 has an O-ring seal 62 to back up its polypack seal 56 in case of failure. If the piston polypack seals 50 fail there is a pressure release tank available to contain the methane gas. There are two pressure gauges 17, 23. If the gauges 17, 23 are reading the same high pressure then the piston polypacks 50 may have been compromised.

Addition of a pressure release tank 26 makes the invention a closed system. The pressure release tank 26 may be an empty methane tank provided by the methane supplier. The pressure release tank can be removed and purged in a safe environment.

The present invention when attached to a HPHT viscometer is not limited to generating and testing the viscosity of just methane/fluids foams/emulsions. It can also be used to test butane/fluids, propane/fluids, ethane/fluids and carbon dioxide/fluids foams/emulsions; and nitrogen gas/fluids foams. The invention can also be attached to lower pressure, lower temperature viscometers 10 to test butane/fluids, propane/fluids, ethane/fluids, $CO_2$/fluids foams/emulsions; and nitrogen gas/fluids and methane gas/fluids foams.

The present invention works because pressure differentials are used to move methane/fluids from one cell into another. That includes both pressure differentials due to the inherent properties of methane and the pressure differentials created by using the pump to drive the piston.

The invention capitalizes on the properties of methane liquid, especially. The vapor pressure of methane liquid at room temperature is high (4600 psi). That means liquid methane has a lot of stored energy that is put to work moving fluids from an area of high pressure to an area of low pressure. In the process methane/fluids get mixed. The valves 18, 19, 20, 21, 22 help to control the direction of movement.

In use, the viscometer cell 10 is first filled with a predetermined amount of fluid and then the invention is attached if there is only one port. (NOTE: If there is only one port available going into the viscometer cell 10 and the port is located at the bottom of the cell, it would be worthwhile to add another needle valve at the base of the viscometer cell so fluids do not leak out when attaching the invention.)

With the constriction member 30 and the un-constricted tubing valve 20 closed, open the valve 19 to the methane tank 16 and pressure up the viscometer cell 10. The needle valve 19 for the methane tank 16 is then closed and the needle valves 18, 22 for the un-constricted tubing and pressure release tank 26 are opened. Methane/fluids from the viscometer cell 10 rush into the piston cell 14, pushing the piston 12 against the stop 42.

Non-pressured, residual water/mineral oil in the piston cell 14 can be used to minimize the piston 12 impact against the stop 42 and can be vented into the pressure release tank 26. The valve 19 for the pressure release tank 26 and the valve 20 for the un-constricted tubing 13 are then closed. The valve 21 to the pump 28 is opened and water/mineral oil pumped by an air driven pump 28, enters the cellar 46 and pushes the piston 12 back forcing the methane and fluids in front of it through the constriction member 30 only using the needle valve 18 in an open state and back into the viscometer cell 10.

Attention must be paid for a pressure spike in the pressure gauge 23 attached to the closed end of the piston cell 14 as this indicates the piston 12 has made contact with the cell plug 52. Immediately shut off the pump 28, close the valve 21 to the pump 28 and close the constriction member 30 needle valve 18. This completes one full cycle of operation.

If more mixing is required begin the cycle again by opening un-constricted needle valve 20 and the valve 22 to the pressure release tank 26. When mixing is completed be sure the constricted tubing needle valve 18 and un-constricted needle valve 20 are closed. The valve to the methane tank 16 should have been closed prior. The viscometer 10 is ready to heat its cell contents and take viscosity readings. Make sure to monitor pressure levels using the pressure gauge 15 of the viscometer cell 10 so that it does not exceed the working pressure of 15000 psi. If higher pressures are generated, then plumbing with autoclave tubing, fittings and needle valves are required.

The constriction member 30 shears the methane/fluids producing foams/emulsions. The tubing 13 and needle valves 18, 19, 20, 21, 22 also provide shear to produce foams/emulsions. The seals 50, 56 are important as they allow pressure differentials to exist. The two polypack seals 50 on the piston 12 face outward from each other so the contents on each side of the piston 12 are isolated from each other. The O-ring seal 62 is a backup for the polypack seal 56 on the cell plug 52. Proper sealing will ensure the safety of the operator. The piston 12 moves fluid with the help of seals 50, 56.

The pressure release tank 26 creates a closed system. Residual water/methane are vented into it and if the piston polypack seals 50 fail, the tank will contain the methane gas. The pressure release tank 26 will have its own valve 22 so that it may be disconnected from the apparatus and its contents can be purged safely.

Without valves 18, 19, 20, 21, 22 the methane/fluids could not be contained and the methane/fluids direction of travel could not be controlled. Needle valves 18, 19, 20, 21, 22, especially, provide additional shear to mix the methane/fluids. The water/mineral oil pumped by the pump 28 will provide the high pressures required to overcome the pressure of methane/fluids on the other side of the piston 12 and will push the piston 12 back to the cell plug 52. The piston cell 14 houses the piston 12 and contains the pressurized and potentially explosive/flammable fluids safely.

The pressure gauge 23 at the closed end of the cell will spike when the piston 12 contacts the cell plug 52. When this happens, the pump 28 is turned off and its associated valve 21 is closed. When both pressure gauges 17, 23 have the same high pressure reading, piston polypacks seals 50 may have been compromised.

The high pressure SS ¼" OD tubing 13, high pressure SS ¼" Swagelok fittings and high pressure SS ¼" female NPT needle valves 18, 19, 20, 21, 22 also function to contain high pressures safely. Their plumbing layout ensures the apparatus works properly.

E. Alternate Embodiments

The invention can be attached to a HPHT viscometer 10 to measure the viscosity of methane/fluids, butane/fluids, propane/fluids, ethane/fluids and carbon dioxide/fluids foams/emulsions and nitrogen gas/fluids foams. It can be attached to a lower pressure, lower temperature viscometer 10 which can then be used to measure the viscosity of butane/fluids, propane/fluids, ethane/fluids and carbon dioxide/fluids foams/emulsions; and nitrogen gas/fluids or methane gas/fluids foams.

The single port design means if you are able to pressure up the viscometer 10, then you should able to attach the invention in many cases. As discussed before, the invention including its cell 14, piston 12, tubing 30, fittings, needle valves 18, 19, 20, 21, 22, and constricted member 30 can be scaled down in volume (as long as all high pressure requirements are met) so that it can be attached to viscometers 10 with smaller sample size.

The piston cell 14 can be constructed with two open ends, but this is not recommended because it means the addition of another cell plug 52 and two additional seals that could leak. The invention may be replaced by a flow through design requiring two ports into and out of the viscometer cell 10, but such designs are more complex with more moving parts making them less safe, less reliable, less adaptable and more expensive. The constriction member 30 can be replaced with a nozzle, sand pack or mixer or any other means of generating shear and stable, homogeneous foams/emulsions.

The pump 28 can be substituted with a pressure tank 29 or air compressor, especially at lower pressures. It can also be substituted with any pump or injection pump driven by an electric motor. The seals 50, 56 could be substituted with a seal material other than viton rubber (such as silicon, VMQ seals which operate over a larger temperature range from very low to very high temperatures). This means the replacement seals 50, 56 could be more compatible with methane, more able to handle higher pressures, more able to handle cold temperatures and/or less prone to failure. The tubing 13, fittings and needle valves 18, 19, 20, 21, 22 can be substituted with higher pressure autoclave tubing 13, fittings and needle valves 18, 19, 20, 21, 22 depending on what test temperatures and pressures are reached.

The pressure release tank 26, which could be an empty methane tank, can also be substituted with a line to a fume hood, a line to the outdoors or by testing outdoors, but this is not recommended. An injection pump or plunger pump (or pump of some other design with or without a piston) might be used to replace the piston equipped cell if it was able to handle methane/fluids and their pressures safely (or not) and if it was equipped with a foam/emulsion generator and with similar plumbing of valves (plumbing of valves that would adapt their pump to serve a similar function to the invention), would be an attempt to copy the invention and would not be as safe. The methane source tank 16 may be a methane gas tank or cryogenic liquid/gas methane tank or tank containing a methane mixture of some sort. The PC-10 viscometer cell 10 may be adapted to fit redundant seals at both its 'plug' end and at its magnet cap end, but would be taking an idea from the invention. A pressure relief valve or high pressure site glass may be added to the invention.

In some embodiments, the piston cell 14 of the present invention may be filled with fluids and pressured up with methane gas or liquid, initially, rather than the viscometer cell 10. The fluids may either be injected into the port 74 on the cell plug 52; or the cell plug 52 can be removed, piston cell 14 then filled with predetermined amount of fluids, then pressured up with methane. Another valve may be required to isolate pressurized contents of invention from viscometer cell 10, until ready for transfer into viscometer cell.

FIGS. 15-19 shows five possible configurations of the invention for attachment to a HPHT viscometer 10 for measuring the viscosity of methane/fluids foams/emulsions, but not limited to just methane. Butane/fluids, propane/fluids, ethane/fluids, carbon dioxide/fluids foams/emulsions; and nitrogen gas/fluids foams can also be contained, generated and tested for viscosity. There are five possible configurations of the invention for attachment to a lower pressure, lower temperature viscometer 10 when testing viscosity of butane/fluids, propane/fluids, ethane/fluids, carbon dioxide/fluids foams/emulsions; and nitrogen gas/fluids and even methane gas/fluids foams.

Figure 15:
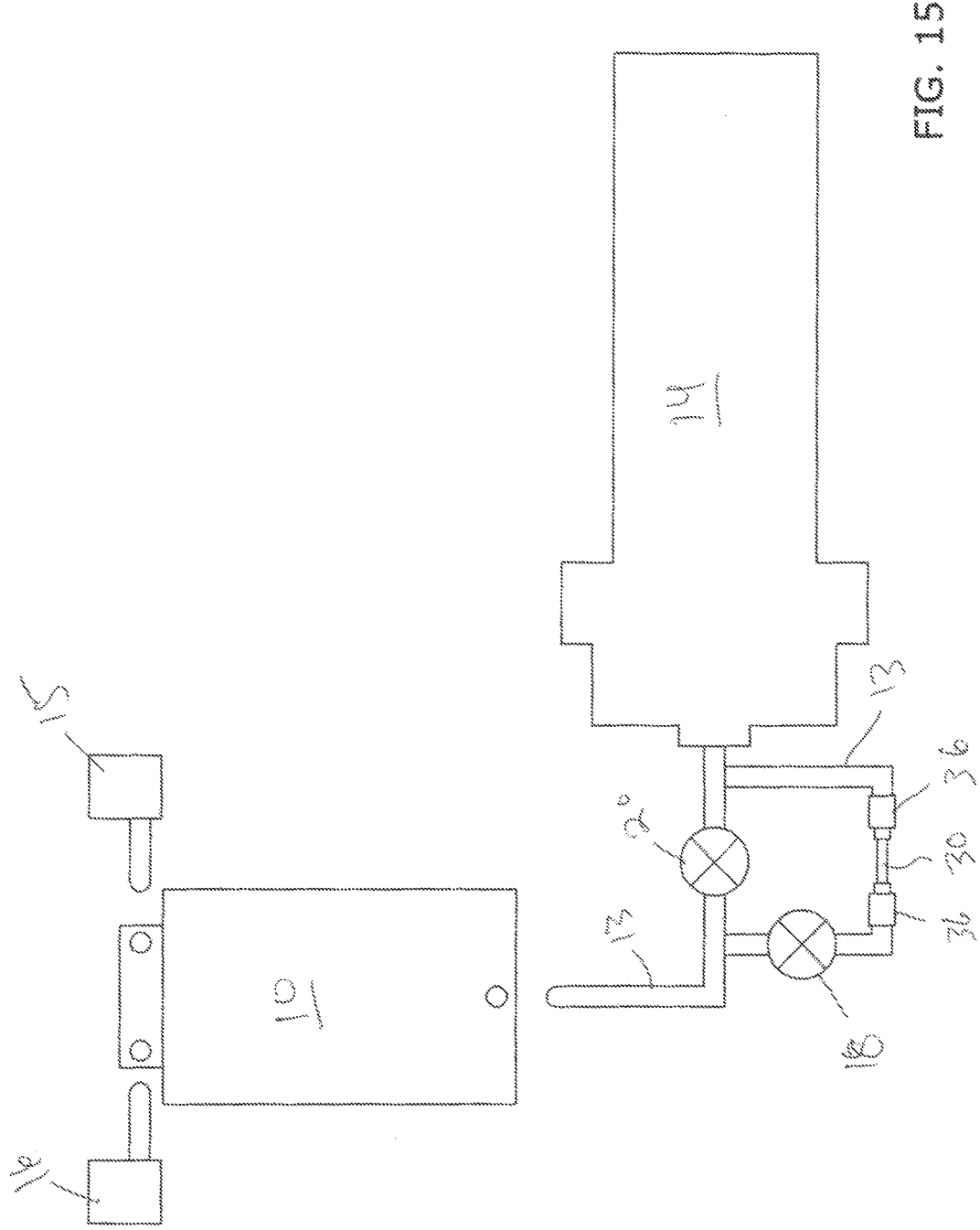
FIG. 15 is a frontal view of the present invention in use with a first viscometer cell.

In the first configuration shown in FIG. 15, the PC-10 viscometer cell 10 has at least three ports available 68, 70, 72. There are two ports 70, 72 on top of the cell 14 and one port 74 at the bottom of the cell 14 making this viscometer 10 very versatile and very adaptable to the invention. One of the top ports 70 can be connected to a methane tank 26 and the second port 72 can be used to attach a pressure gauge 23. The third bottom port (the flow through bolt) can be attached to the invention. The pressure gauge 15 and needle valve to the methane tank 16 can be omitted from the invention.

Figure 16:
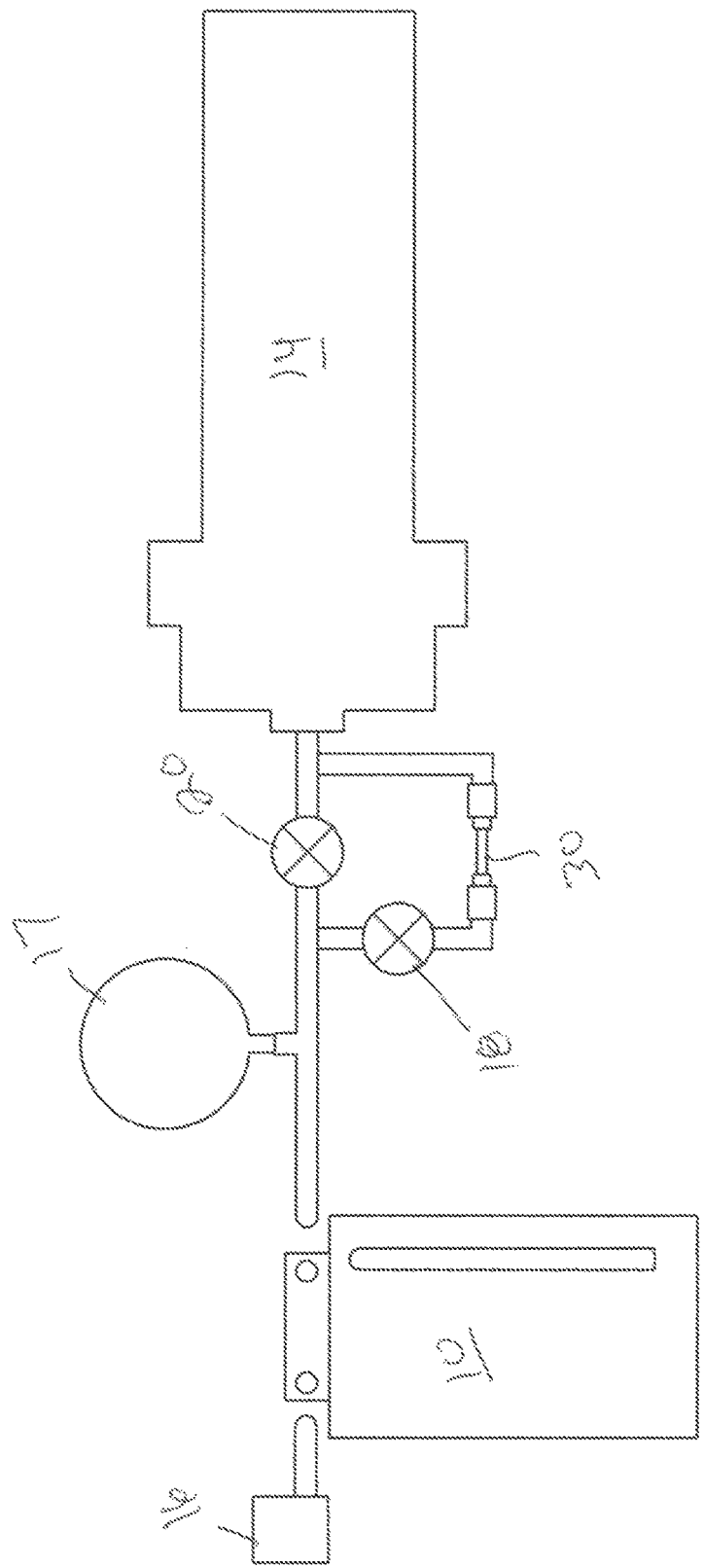
FIG. 16 is a frontal view of the present invention in use with a second viscometer cell.

In the second configuration shown in FIG. 16, if the viscometer cell has two ports 70, 72 on top available, then one port 70 can be used to pressure up with methane and the second port 72 will be attached to the invention using a siphon tube. The needle valve to the methane tank 16 can be omitted from the invention.

Figure 17:
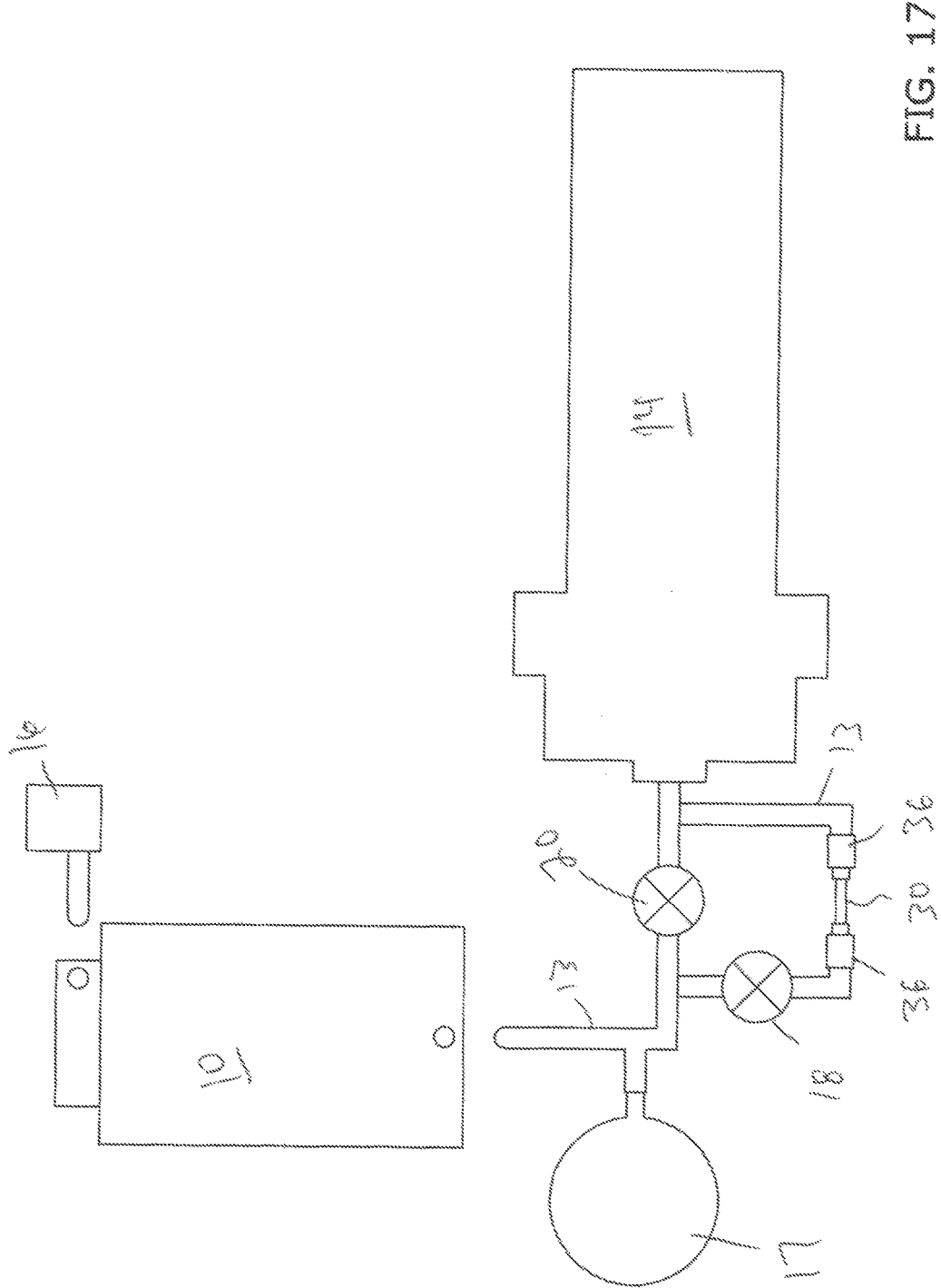
FIG. 17 is a frontal view of the present invention in use with a third viscometer cell.

In the third configuration shown in FIG. 17, the viscometer cell 10 has one port on the bottom and one port on the top available, the port on top can be used to pressure up with methane and the port on the bottom is attached to the invention. The needle valve to the methane tank 16 can be omitted from the invention.

Figure 18:
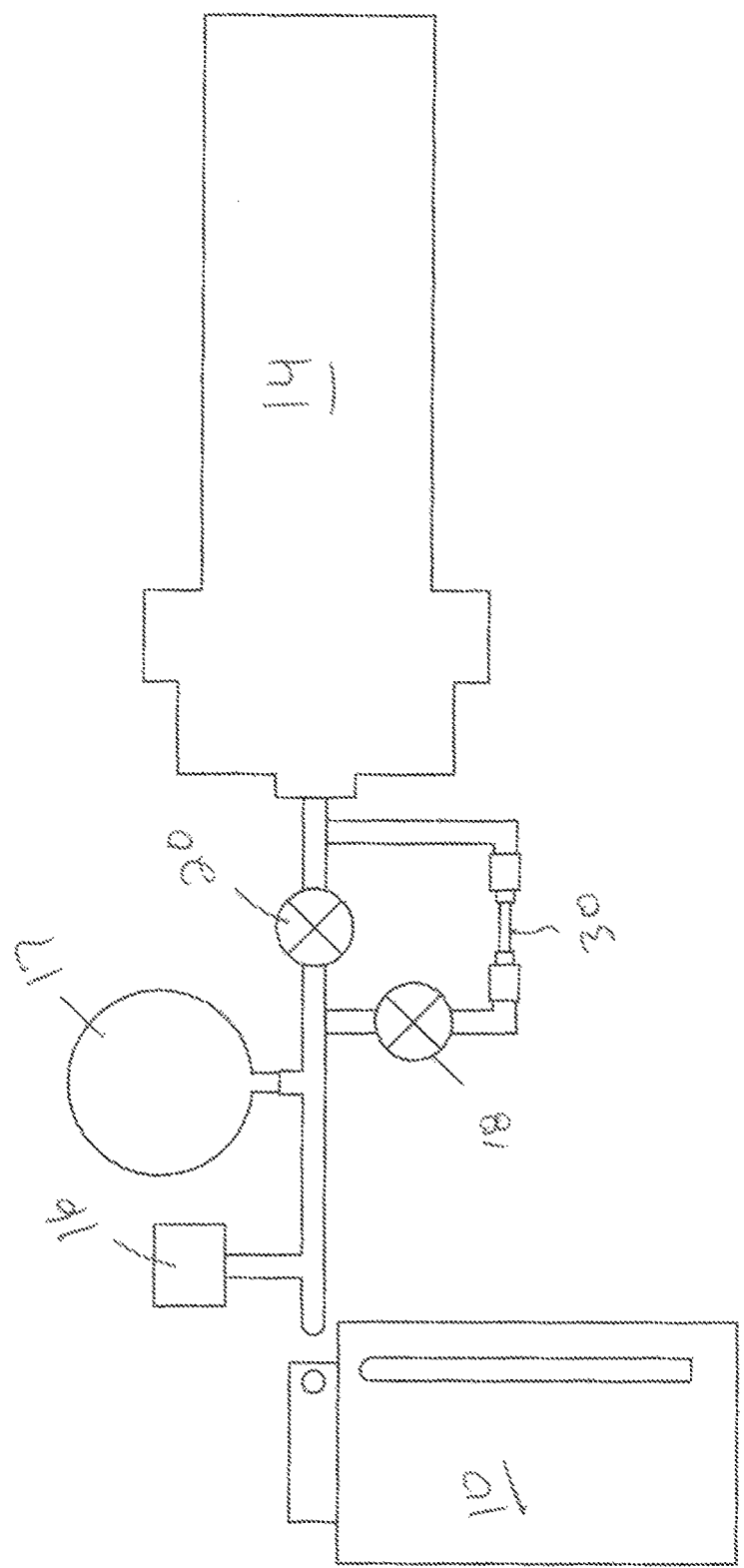
FIG. 18 is a frontal view of the present invention in use with a fourth viscometer cell.
Figure 19:
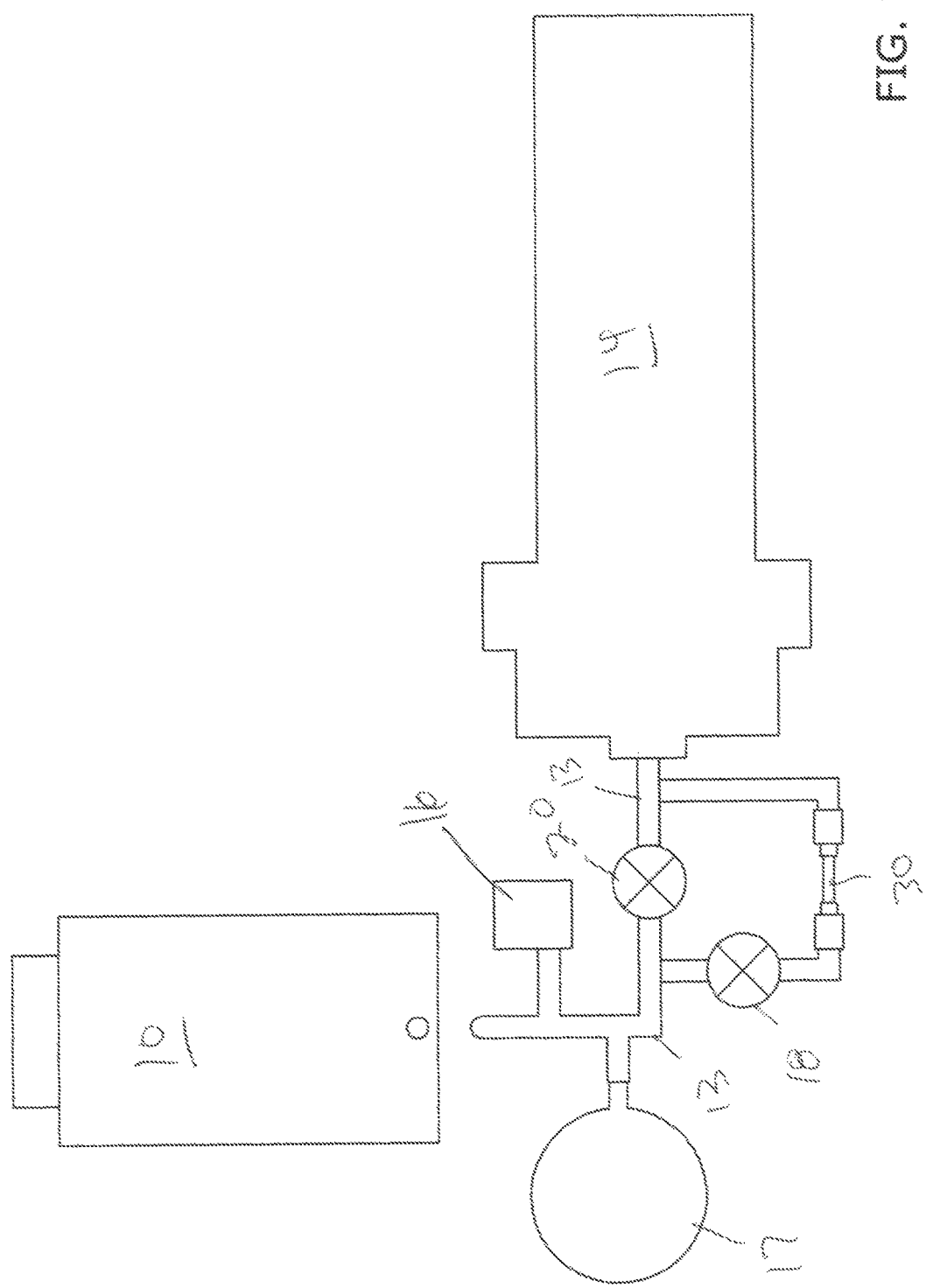
FIG. 19 is a frontal view of the present invention in use with a fifth viscometer cell.

In the fourth configuration shown in FIG. 18, if the viscometer cell 10 has only one port on top, the invention can be connected to this port using a siphon tube. In the fifth configuration shown in FIG. 19, if the viscometer cell has only one port on the bottom, the invention can be connected to this port. It would be worthwhile to add another needle valve to the bottom of the port so that fluids do not leak out when connecting the invention.

There is also a sixth possible configuration where one or more of the present invention(s) are attached end-to-end for production of methane foams/emulsions before attachment to the viscometer cell 10. Only one of the piston cells 14 is filled with a predetermined volume of fluids and pressured up with methane gas or liquid.

The methane/fluids are moved from one piston cell 14 to the other until homogeneous methane foams/emulsions are formed. The methane/fluids will be sheared when moved between the two piston cells 14 only. This will allow pre-sheared, homogeneous methane foams/emulsions to be injected into the viscometer cell 10 and then the invention(s) can be detached from the viscometer 10. This will increase adaptability to additional viscometers 10 on the market. After the methane foams/emulsions are injected into the viscometer cell 10, the invention(s) are detached from the viscometer cell 10. An extra valve will be required on the invention(s) to accomplish this.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A viscometer cell attachment device, comprising:
   a viscometer cell for storing a substance, wherein the substance comprises methane;
   a piston cell having a first end and a second end, the first end of the piston cell being fluidly connected with the viscometer cell such that the substance may enter the piston cell from the viscometer cell or exit the piston cell to the viscometer cell;
   a first channel extending from said first end of said piston cell;
   a second channel extending from said second end of said piston cell, wherein said second channel is narrower than said first channel;
   a piston movably positioned within said first channel, wherein the piston is free-floating within the first channel;
   a cell plug removably secured to said first end of said piston cell;
   a constriction member positioned near said second end of said piston cell, the constriction member being adapted to generate shear to produce a foam or emulsion of the substance; and
   a plurality of ports on said piston cell.

2. The viscometer cell attachment device of claim 1, wherein said plurality of ports includes a first port adapted for connection to a pressure gauge.

3. The viscometer cell attachment device of claim 2, wherein said plurality of ports includes a second port adapted for connection to a pressure release tank.

4. The viscometer cell attachment device of claim 3, wherein said plurality of ports includes a third port adapted for connection to a pump.

5. The viscometer cell attachment device of claim 1, wherein said cell plug includes a polypack seal.

6. The viscometer cell attachment device of claim 5, wherein said cell plug includes an O-ring seal.

7. The viscometer cell attachment device of claim 1, wherein said piston includes a first groove near its first end and a second groove near its second end.

8. The viscometer cell attachment device of claim 7, including a first seal positioned in said first groove and a second seal positioned in said second groove.

9. The viscometer cell attachment device of claim 8, wherein said first seal and said second seal are each comprised of a polypack seal.

10. The viscometer cell attachment device of claim 1, wherein said piston cell includes a plurality of valves.

11. The viscometer cell attachment device of claim 10, wherein said plurality of valves includes a first valve for controlling flow between said piston cell and a methane tank.

12. The viscometer cell attachment device of claim 11, wherein said plurality of valves includes a second valve for controlling flow through said constriction member.

13. The viscometer cell attachment device of claim 12, wherein said plurality of valves includes a third valve for controlling flow out of said second end of said piston cell.

14. A viscometer cell attachment system, comprising:
   a viscometer cell for storing a substance, the substance selected from the group consisting of methane, butane, propane, ethane, nitrogen, and carbon dioxide;
   a piston cell having a first end and a second end, wherein the piston cell comprises a first port, a second port, and a third port, the first end of the piston cell being fluidly connected with the viscometer cell such that the substance may enter the piston cell from the viscometer cell or exit the piston cell to the viscometer cell;
a first channel extending from said first end of said piston cell;
a second channel extending from said second end of said piston cell, wherein said second channel is narrower than said first channel;
a piston movably positioned within said first channel, wherein the piston is free-floating within the first channel;
a cell plug removably secured to said first end of said piston cell, wherein the cell plug comprises a collar and a crown, wherein the collar extends outwardly from the collar crown;
a constriction member positioned near said second end of said piston cell, the constriction member being adapted to generate shear to produce a foam or emulsion of the substance;
an O-ring seal positioned between the piston cell and the cell plug;
a pressure gauge connected to the first port of the piston cell;
a pressure release tank connected to the second port of the piston cell; and
a pump connected to the third port of the piston cell.

15. The viscometer cell attachment device of claim 14, wherein said cell plug includes a polypack seal.

16. A method of testing viscosity of a substance, comprising:
storing a volume of the substance in a viscometer cell;
transferring the substance from the viscometer cell to a piston cell, wherein the piston cell comprises:
a first channel extending from a first end of the piston cell;
a second channel extending from a second end of the piston cell, wherein the second channel is narrower than the first channel;
a piston movably positioned within the first channel;
a cell plug removably secured to the first end of the piston cell;
a constriction member positioned near the second end of the piston cell;
a plurality of ports; and
a plurality of seals;
generating an emulsion or foam by shearing the substance with the constriction member; and
returning the substance to the viscometer cell.

17. The method of claim 16, wherein the substance is selected from a group consisting of methane, butane, propane, ethane, nitrogen, and carbon dioxide.

18. The method of claim 16, wherein the substance is comprised of methane.

19. The method of claim 16, wherein the plurality of seals comprise a polypack seal and an O-ring seal.

* * * * *